United States Patent [19]

Cercone

[11] Patent Number: 6,099,952
[45] Date of Patent: Aug. 8, 2000

[54] MEDICAL SPONGE HAVING MUCOPOLYSACCHARIDE COATING

[75] Inventor: Ronald J. Cercone, Easy Lyme, Conn.

[73] Assignee: Xomed Surgical Products, Inc., Jacksonville, Fla.

[21] Appl. No.: 09/025,546

[22] Filed: Feb. 18, 1998

[51] Int. Cl.[7] .................... A61K 9/00; A61F 13/00; B32B 5/00
[52] U.S. Cl. ................... 428/308.4; 428/318.4; 428/319.3; 424/78.06; 424/488; 604/369; 604/385.1; 427/2.31
[58] Field of Search ........................................ 428/308.4

[56] References Cited

U.S. PATENT DOCUMENTS

| | | | |
|---|---|---|---|
| 1,002,842 | 9/1911 | Harriss | 19/54 |
| 1,002,913 | 9/1911 | Harriss | 19/54 |
| 1,094,361 | 4/1914 | Blevney | 15/230.16 |
| 1,775,186 | 9/1930 | Bartling | 15/97.1 |
| 2,053,604 | 9/1936 | Dullinger | 492/31 |
| 2,485,428 | 10/1949 | Bleier et al. | 401/218 |
| 2,609,347 | 9/1952 | Wilson | 521/87 |
| 2,932,859 | 4/1960 | Rockoff | 19/258 |
| 3,566,871 | 3/1971 | Richter et al. | 604/362 |
| 3,837,950 | 9/1974 | Reimels | 156/73.2 |
| 3,858,329 | 1/1975 | Koide et al. | 34/265 |
| 3,915,671 | 10/1975 | Kagawa | 51/296 |
| 4,098,728 | 7/1978 | Rosenblatt | 521/141 |
| 4,566,911 | 1/1986 | Tomita et al. | 134/6 |
| 4,807,339 | 2/1989 | Hayashi | 492/24 |
| 4,851,521 | 7/1989 | della Valle et al. | 536/55.1 |
| 4,925,453 | 5/1990 | Kannankeril | 604/378 |
| 5,009,652 | 4/1991 | Morgan et al. | 604/385.01 |
| 5,071,648 | 12/1991 | Rosenblatt | 424/78.06 |
| 5,196,185 | 3/1993 | Silver et al. | 424/45 |
| 5,387,206 | 2/1995 | Valentine et al. | 604/358 |
| 5,414,914 | 5/1995 | Suzuki et al. | 28/105 |
| 5,466,231 | 11/1995 | Cercone et al. | 604/369 |
| 5,469,864 | 11/1995 | Rosenblatt | 128/849 |
| 5,502,081 | 3/1996 | Kuo et al. | 514/777 |
| 5,503,848 | 4/1996 | Perbellini et al. | 424/488 |
| 5,510,418 | 4/1996 | Rhee et al. | 525/54.2 |
| 5,524,642 | 6/1996 | Rosenblatt | 128/849 |
| 5,556,391 | 9/1996 | Cercone et al. | 604/369 |
| 5,644,049 | 7/1997 | Giusti et al. | 536/53 |
| 5,766,631 | 6/1998 | Arnold | 424/486 |
| 5,843,060 | 12/1998 | Cercone | 604/36.9 |
| 5,928,665 | 7/1999 | Cercone | 424/445 |

FOREIGN PATENT DOCUMENTS 13301  11/1885  United Kingdom.

*Primary Examiner*—Ellen M. McAvoy

[57] ABSTRACT

A sponge consisting of a sponge material, such as a polyvinyl alcohol sponge material having a coating of a non adherent mucopolysaccharide, hyaluronic acid ester. The ester can be applied to surfaces of the sponge or can be a uniformly dispersed interstitial gel of an esterified mucopolysaccharide, such as hyaluronic acid, formed by cross linking polyvinyl alcohol with various organic compounds containing carbonyl groups in the presence of acid catalysts, and reacting unreacted portions of the polyvinyl alcohol with the mucopolysaccharide to esterify the mucopolysaccharide and copolymerize the ester with the polyvinyl alcohol.

14 Claims, No Drawings

MEDICAL SPONGE HAVING MUCOPOLYSACCHARIDE COATING

BACKGROUND OF THE INVENTION

1. Field of the Invention

The invention relates to medical sponges. More specifically, the invention is a medical sponge with reduced sticking properties and a method of making such a sponge.

2. Description of the Related Art

Medical sponges are widely used as bandages, diagnostic swabs, as surgical sponges for orthopedic, plastic, eye, ear, nose and throat procedures, as well as in other applications. For example, it is known to use medical sponges as surgical packing or dressings. During many surgical procedures, for example procedures in the anatomical cavity, sponges are used to absorb blood and to isolate the various organs from the operating field. The latter is accomplished by packing the organs with sponges to restrain them from interfering with the operation. In nasal and sinus procedures, sponges are used as packings to prevent excessive bleeding and swelling and often are left in place for several days or even weeks.

A condition known as "sticking" renders it difficult to remove packings constituted of conventional medical sponges because the sponges tend to adhere to tissue. Several primary factors cause adhesion. First, adhesion results from the healing process where tissue grows into the structure of the sponge used as packing material or a dressing. Healing adhesion is a particular problem when packing the mucosal linings of nasal or sinus passages. Second, difficulty in removing packings from nasal and sinus passages, or other small passages, arises from the relatively small cross sectional area of the passages and the resulting frictional resistance of the packing as it passes through the passage. Third, dried blood and other exudate in and around a wound tend to dry in place, thereby binding a sponge used as dressing to the wound.

A common surgical sponge is made of a cellulose material. Also, gauze pads and polyurethane materials are used for surgical sponges. More recently, a sponge material made from a reaction of polyvinyl alcohol (or polyvinyl acetal) and an aldehyde (such as formaldehyde) has been used. This sponge material, known as a PVA sponge material and sold by Merocel Scientific Products, is absorbant and low in particulate matter. The PVA sponge can be formed by reacting polyvinyl alcohol and an aqueous formaldehyde solution in the presence of an acid catalyst under carefully controlled conditions to produce a sponge material suitable for medical use and having controlled pore size uniformly distributed throughout its volume. The PVA sponge is expandable, biocompatible, absorbent, lint free, soft, and fast wicking.

Instantaneous wicking and high liquid holding capacity is attained by controlling the temperature and time conditions and processing procedure by which the formaldehyde and the polyvinyl alcohol are mixed and reacted. The formaldehyde and polyvinyl alcohol are heated and mixed in the presence of a surfactant to entrain an inert gas and to form pores of a uniform size. After a reaction, the sponge material is heated to cure the outer surface thereof and thus retain a stable overall shape. Thereafter, the sponge material is cured so that the sponge material experiences minimum shrinkage during the curing cycle. The cured sponge is then washed to remove unreacted chemical residue. The sponge material can be frozen and cut to shape for various applications. Pore size can be controlled through mixing or straining the mixture prior to curing. The PVA sponge and a method of making the PVA sponge is described in U.S. Pat. No. 4,098,728 issued to Rosenblatt, the disclosure of which is incorporated herein by reference. The PVA sponge, similar to other surgical sponges, is subject to sticking.

The use of coatings, films, and woven fibers of hyaluronic acid and its derivatives is also well known in various medical applications. Hyaluronic acid is a linear polymer present in the pericellular gels of connective tissues of vertebrates, articular synovial liquid, the vitreous humor, the tissue of the human umbilical cord, and cock's combs. For example, hyaluronic acid is known to lack inflammatory activity and is therefore useful to facilitate cicatrization, to replace endobulbar fluids, and for joint therapy. Also, it is known that hyaluronic acid promotes tissue repair. Esters of hyaluronic acid are known to be useful in cosmetic applications and for forming biodegradable plastics. U.S. Pat. No. 5,503,848 issued to Perbellinni et al discloses various applications for hyaluronic acid and esters thereof, as well as a "spongy" material made essentially of hyaluronic acid. However, previously, hyaluronic acid and its esters have not been combined with surgical sponges used as packings and dressings.

Overlays of silk, rubber, and the like, and coatings of materials such as polyethylene, lubricating gels and cremes have been used to alleviate patient discomfort upon withdrawal of packings. However, sticking of packing and dressings is still a problem.

SUMMARY OF THE INVENTION

It is an object of the invention to eliminate sticking of surgical packing and dressings due to adhesion of the packing and dressings to tissue.

It is another object of the invention to facilitate removal of packing in nasal and sinus passages, and other small passages, by increasing the lubricity of the packing.

It is another object of it the invention to combine an ester of hyaluronic acid with a polyvinyl alcohol sponge material.

To achieve these objects, a first aspect of the invention is a synthetic sponge material having a coating of a non adherent mucopolysaccharide such as a hyaluronic acid ester. A second aspect of the invention is a polyvinyl alcohol sponge material containing a uniformly dispersed interstitial gel of an esterified mucopolysaccharide such as hyaluronic acid. A third aspect of the invention is a method of forming a synthetic sponge material including the steps of cross linking polyvinyl alcohol with various organic compounds containing carbonyl groups (such as aldehydes) in the presence of an acid catalyst, and reacting unreacted portions of the polyvinyl alcohol with a mucopolysaccharide such as hyaluronic acid to esterify the mucopolysaccharide and copolymerize the ester with the polyvinyl alcohol.

DETAILED DESCRIPTION OF THE PREFERRED EMBODIMENTS

The invention is a sponge useful for forming various surgical packings and dressings. However, the sponge of the invention can be used in various applications in the field of medical science and other fields. The term "packing" as used herein refers to any material used to fill a natural anatomical cavity or wound or to hold organs or other tissue in a desired position. The term "dressing" as used herein refers to any material that is to be applied to a wound for protection, absorbance, drainage, or the like. The phrase "sponge material" as used herein refers to a base material, such as a PVA sponge material. The term "sponge" as used herein refers to the sponge material combined with a mucopolysaccharide.

U.S. Pat. No. 4,098,728 issued to Rosenblatt, the disclosure which is incorporated herein by reference, discloses a method of making a PVA sponge material. A first sponge according to the invention is a PVA sponge material coated with a hyaluronic acid ester. The sponge material is formed in a conventional manner, such as that disclosed in the above-noted patent. Subsequently, the sponge material is cut into the final product shape. Alternatively, the sponge material can be molded into the desired final product shape. The sponge material is then coated with a solution of hyaluronic acid ester in water at a concentration of about 0.20%–0.80% by volume. The coating can be applied in any known manner, such as roller coating, atomized spraying, dipping, or painting. The precise concentration is selected in consideration of ease of application, not effectiveness, because very low concentrations (e.g. 0.2%) are effective to eliminate sticking. For example, if a gel is desired to spread a thin coating, a high concentration, e.g. 40%–80% of the hyaluronic acid ester is selected. On the other hand, if an atomized spray or dipping method is used, the concentration is lower, e.g. 0.20%–1.0% to lower the viscosity of the hyaluronic acid ester solution and facilitate application thereof to the sponge material.

A second sponge according to the invention is a copolymer of PVA and a mucopolysaccharide such as a hyaluronic ester. The sponge is produced by cross-linking polyvinyl alcohol with various organic compounds containing carbonyl groups, such as aldehydes and/or carboxylic acids. "Cross linking" is the formation of ester bonding between chains of adjacent hydroxyl groups. During the primary reaction of the polyvinyl alcohol with the organic compound, a secondary reaction is allowed to proceed as an esterification of the mucopolysaccharide. In the secondary reaction, portions of the unreacted sites of the polyvinyl alcohol form an ester of the mucopolysaccharide. The primary and secondary reactions occur substantially simultaneously and the two materials, polyvinyl alcohol and the mucopolysaccharide are both physically and chemically bound while intimate mixing occurs. The primary cross-linking reaction is allowed to proceed until about 10% to 35% of the available active sites of the polyvinyl alcohol are bound. At this point of the primary reaction, generally ocurring after the first 5 to 15 seconds of the cross-linking reaction, the mucopolysaccharide is added before the polyvinyl alcohol is fully cross-linked to permit the secondary reaction, the esterification of the mucopolysaccharide, to occur in-situ.

The addition of the mucopolysaccharide at the precise time, causes esterification of the mucopolysaccharide and interstitial formation of micro clusters of the ester within the structure of the partially cured polyvinyl alcohol mixture. Apparently, the polyvinyl alcohol acts as a partial polymeric bridge of the esters formed, since the esters are reaction products of the polyvinyl alcohol and the hyaluronic acid. The same polymer chain of polyvinyl alcohol reacts with the aldehyde and the hyaluronic acid. Therefore, some chemical cross bonding occurs between the polyvinyl alcohol and the ester of hyaluronic acid. However, most of the hyaluronic acid esters formed by the second reaction is held within the pores of the polyvinyl alcohol sponge material as micro clusters. The presence of the hyaluronic acid ester within the structure of the polyvinyl alcohol sponge imparts the desired lubricity and adhesion resistance to the resulting sponge. In this sponge, a uniformly dispersed gel of the hyaluronic acid ester exists, in the form of micro clusters, throughout the polyvinyl alcohol sponge material. The reaction is halted at the desired time by washing the sponge with water, for example when approximately 30 to 50 percent of the active sites are bound. This amount of cross-linking is desirable to maintain the flexibility of the final sponge.

The following is an example of a process for forming the sponge of the invention. Two solutions of polyvinyl alcohol, at a concentration 5%–30% by weight in water were mixed with an acid catalyst and an aldehyde respectively. The two solutions were mixed together into a combined solution rapidly with high shear while incorporating inert gases for pore formation to allow a primary cross-linking reaction to occur between the polyvinyl alcohol and the aldehyde. During the mixing of the combined solution, at a point corresponding to 10%–35% of cross-linking, i.e. binding, of hydroxyl groups of the polyvinyl alcohol and the aldehyde, a solution of hyaluronic acid at a concentration of 0.1%–0.80% is added to the combined solution to begin the secondary cross-linking of the hyaluronic acid and the polyvinyl alcohol. The volume of the third solution, the hyaluronic acid, was limited to a maximum of five to ten percent of the total volume of the combined solution and the hyaluronic acid solution. Wetting aides, such as detergents, TRITON-X, TWEEN 20-80, poloxamers, and the like, can be added at this time or at any appropriate step of the process. The inclusion of the inert gas produces a frothed foam which is delivered to a container, or mold, for final curing and cross-linking. After a time period of 3 to 48 hours of curing at a temperature in the range of 60° F.–150° F., the cured material is washed with water to remove all reactants, thereby halting the progress of the reaction, i.e. the cross-linking. The final configuration of the product made from the sponge may be determined either by the shape of the container or by cutting the molded sponge into the final desired shapes with dyes or other known cutting equipment Because the sponge of the invention is coated or impregnated with an ester of hyaluronic acid, packings and dressings formed from the sponge are more lubricious and less susceptible to in-growth. Therefore adherence to tissue, and thus sticking, is minimized.

The sponge of the invention can be used for forming nasal and sinus packings of any shape and size. Further, the sponge can be used to form packings or dressings or any type for surgical or other medical applications. The sponge of the invention can be used in any application and is particularly suited to applications where non-adherence to tissue or other material is desirable. The sponge can be molded, cut, or otherwise formed to any desired shape and size and can be combined with other elements, such as adhesive strips, handles, manipulating members or the like. The concentration, temperatures, time durations, and degree of cross-linking as well as the particular chemicals and other parameters in the sponge forming process can be varied to suit the desired characteristics of the sponge. For example, various aldehydes and acids can be used to react with the polyvinyl alcohol. The hyaluronic acid, or other mucopolysaccharide, can be introduced into the sponge material in any manner.

The embodiments and examples described above are not to be construed as limiting the scope of the invention as defined by the appended claims.

What is claimed is:

1. A sponge having decreased tissue adhesion characteristics and a high lubricity, said sponge being suitable for use as packings for anatomical tissue and as dressings for wounds, said sponge being easily removed from the tissue or wound with minimum trauma to the tissue or wound, said sponge material comprising:

a polyvinyl alcohol sponge material; and a mucopolysaccharide chemically bonded by an esterification reaction with hydroxyl groups comprising portions of said sponge material.

2. The sponge as recited in claim 1, wherein said mucopolysaccharide is hyaluronic acid or derivative.

3. A method of forming a sponge having decreased tissue adhesion characteristics and a high lubricity, said sponge being suitable for use as packings for anatomical tissue and as dressings for wounds, said sponge being easily removed from the tissue or wound with minimum trauma to the tissue or wound, said method comprising the steps of:

forming a polyvinyl alcohol sponge material; and reacting a mucopolysaccharide with unreacted hydroxyl groups on the polyvinyl alcohol sponge material.

4. A method as recited in claim 3, wherein said mucopolysaccharide is a hyaluronic acid.

5. A method as recited in claim 3, wherein said forming step comprises mixing a polyvinyl alcohol solution with an acid catalyst and an organic compound containing carbonyl groups to form a mixture and conducting a primary cross-linking reaction between portions of the polyvinyl alcohol and the organic compound.

6. A method as recited in claim 5, wherein said reacting step comprises introducing the mucopolysaccharide into the mixture and permitting a secondary cross-linking esterification reaction between unreacted portions of the polyvinyl alcohol and the mucopolysaccharide.

7. A method as recited in claim 6, wherein said reacting step is initiated after 10%–35% of hydroxyl groups of the polyvinyl alcohol are cross-linked during the primary cross-linking reaction.

8. A method as recited in claim 7, wherein said mucopolysaccharide comprises a hyaluronic acid solution at a concentration of 0.1%–0.80% by weight.

9. A method as recited in claim 8, wherein the hyaluronic acid solution is 5%–10% inclusive of the total solution volume.

10. A method as recited in claim 9, further comprising the steps of: curing the sponge material; and washing the cured sponge material.

11. A sponge having decreased tissue adhesion characteristics and a high lubricity, said sponge being suitable for use as packings for anatomical tissue and as dressings for wounds, said sponge being easily removed from the tissue or wound with minimum trauma to the tissue or wound, said sponge material comprising:

a sponge material; and a mucopolysaccharide coated on surfaces of said sponge material and impregnated in pore spaces of said sponge material.

12. The sponge as recited in claim 11, wherein said mucopolysaccharide is hyaluronic acid.

13. The sponge material as recited in claim 11, wherein said sponge material is a synthetic sponge material.

14. The sponge material as recited in claim 11, wherein said sponge material is a polyvinyl alcohol sponge material.

\* \* \* \* \*